United States Patent [19]

Hai et al.

[11] Patent Number: 5,013,866

[45] Date of Patent: May 7, 1991

[54] PHARMACEUTICAL GRADE 3,5-DIBROMOSALICYLIC ACID AND METOHD FOR SYNTHESIZING SAME

[75] Inventors: Ton T. Hai, Lake Villa; Deanna J. Nelson, Libertyville, both of Ill.

[73] Assignee: Baxter International Inc., Deerfield, Ill.

[21] Appl. No.: 442,039

[22] Filed: Nov. 28, 1989

[51] Int. Cl.$^5$ .............................................. C07C 65/00
[52] U.S. Cl. .................................................... 562/474
[58] Field of Search ......................................... 562/474

[56] References Cited

U.S. PATENT DOCUMENTS 3,381,032  9/1965  Surine et al. ......................... 562/474

FOREIGN PATENT DOCUMENTS 6610859  8/1966  Netherlands .

OTHER PUBLICATIONS

Haksar et al., Vikram J., Vikram Univ., 6:67 (1962).

Primary Examiner—Paul J. Killos
Attorney, Agent, or Firm—Sarah E. Bates; Paul C. Flattery; Robert E. Hartenberger

[57] ABSTRACT

An improved method of synthesizing 3,5-dibromosalicylic acid provides a highly purified pharmaceutical grade product free of toxic by-products and solvents. The purified product may be utilized as an intermediate in synthesizing pharmaceutical grade substances, as a bactericide when incorporated into topical ointments, and as an adjuvant in drug absorption systems.

6 Claims, No Drawings

PHARMACEUTICAL GRADE 3,5-DIBROMOSALICYLIC ACID AND METOHD FOR SYNTHESIZING SAME

FIELD OF THE INVENTION

The present invention relates to highly purified 3,5-dibromosalicylic acid and a new method of preparing it.

BACKGROUND OF THE INVENTION

Chemically modified hemoglobins present an important approach to providing alternatives to transfusion of donated blood. Chemical modifications, chiefly by treatment with cross-linking agents, prevent tetrameric hemoglobin from dissociating into dimers which leads to rapid renal elimination. These dimers also may cause kidney damage. Cross-linked hemoglobin has been previously described for alpha, alpha cross-linkages in U.S. Pat. Nos. 4,598,064 and 4,600,531 (Walder) where the alpha chains are cross-linked by use of the cross-linking agent bis (3,5-dibromosalicyl) fumarate.

The use of cross-linking agents in preparing modified hemoglobins for therapeutic administration requires that the cross-linking agent and its precursors be of pharmaceutical purity. This means that a method of synthesizing the cross-linking agent or its precursors must not yield by-products that co-purify with the desired compound thereby risking contamination of the final hemoglobin. By pharmaceutical purity, it is meant that the substance be substantially free of any toxic compound. In general, a cross-linking agent of choice is formed in a reaction generalized in the following equation:

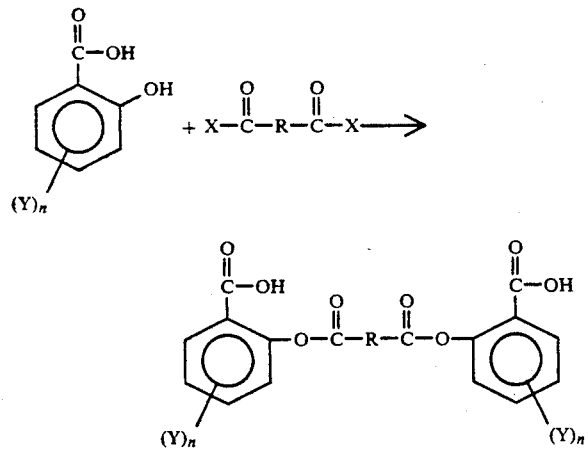

wherein R is a lower alkyl or alkylene of from 1 to about 5 carbon atoms; Y is hydrogen, chloro-, bromo-, iodo-, nitro-, cyano- or trifluoromethyl-, and n is 1 or 2. Particularly efficacious in this reaction is 3,5-dibromosalicylic acid.

3,5-dibromosalicylic acid is also an important precursor in the synthesis of 3,5-dibromoacetylsalicylic acid. This compound is the dibrominated derivative of aspirin, and like aspirin, exhibits analgesic and anti-inflammatory properties. The di-aspirin derivatives have also been evaluated as potential anti-sickling agents. See Thompson et al., Res. Comm. in Chem. Path and Pharm., 48:381 (1985) and Walder et al., PNAS, 74:5499 (1977). In combination with glucose and sodium acetate or citrate, dibromoaspirin may significantly reduce gastrointestinal mucosal damage, as disclosed in U.S. Pat. No. 4,440.762 (Rainsford). 3,5-dibromoacetylsalicylic acid can be conveniently synthesized from dibromosalicylic acid and acetic anhydride in the presence of sodium acetate in water.

The synthesis of 3,5-dibromosalicylic acid has been described heretofore. U.S. Pat. No. 3,426,035 discloses a method of brominating salicylic acid utilizing epichlorohydrin or a lower alkylene oxide as an acid receptor in the nuclear bromination of aromatic compounds generally. A melting point of 221°-223.5° C. was reported. A second method in which the reaction is carried out in 50 percent paradioxane yields 3,5-dibromosalicylic acid with a reported melting point of 226.5°-228° C. (Neth. Applic. No. 6,610,859). In a third method described by Haksar et al., Vikram J., Vikram Univ., 6:67 (1962), salicylic acid is reacted with bromine in a medium of hot glacial acetic acid to yield a product with a melting point of 221° C. All of these methods yield a product with melting points in the range of 221°-228° C., and all contain various impurities, principally monobrominated salicylic acid or decarboxylated brominated phenol.

Another disadvantage of prior art methods is the difficulty of removing the toxic solvents in the which bromination reaction is carried out. Although the bromination reaction can be more readily controlled in the presence of such solvents, these methods without further extensive purification steps are not useful for production of pharmaceutically acceptable material because of the risk of carry-over of toxic contaminants. In particular, methods utilizing paradioxane are unsuitable in pharmaceutical applications. Glacial acetic acid, utilized as a reaction medium by Haksar, is impractical in large-scale production because of the prohibitive expense of removing it. Finally, these methods are disadvantageous because the relatively high temperature conditions of bromination promote decarboxylation. In an industrial context, high temperature reflux procedures utilizing such flammable media also create a fire hazard and potential for escape of noxious fumes.

In addition to its usefulness as an intermediate in chemical syntheses, 3,5-dibromosalicylic acid has a number of direct applications where pharmaceutical purity is desirable. The compound is a member of a class of salicylates utilized singly or in combination as topical bactericides, fungicides, and treatment agents for various skin conditions. 3,5-dibromosalicylic acid is listed in the Merck Index (10th ed.) as a bactericide for this purpose. Direct topical compositions ideally should not contain impurities such as toxic solvents which may be absorbed through the skin. In other pharmaceutical applications the compound is used as a promoter of protein absorption in enteral administration (EP2251-89A2, Davis) and as an adjuvant in rectal drug delivery systems, as disclosed in U.S. Pat. Nos. 4,406,896 and 4,464,363 (Higuchi).

SUMMARY OF THE INVENTION

This invention is 3,5-dibromosalicylic acid which sublimes at temperatures greater than about 180° C. It is further substantially homogeneous by chromatographic analysis. The compound is produced by a method comprising the steps of reacting bromine with salicylic acid in a solution of aqueous alcohol, maintaining the temperature of the reaction mix below about 40° C., and optionally, further purifying by subliming and recovering the sublimate. This ultrapure dibromosalicylic acid is especially suited for production of cross-linked hemoglobin, dibrominated aspirin, or for direct administration in drug administration systems and topical applications.

DETAILED DESCRIPTION OF THE PREFERRED EMBODIMENT

The compound of this invention contains virtually no contaminants, no traces of any solvents, and has the unexpected property of subliming at a temperature above 180° C. rather than melting. In the method of the present invention, liquid bromine is added to salicylic acid contained in a solution of an aqueous alcohol. The desired product, 3,5-dibromosalicylic acid, precipitates immediately upon formation, thereby preventing secondary decarboxylation to 2,4,6-tribromophenol. Following recrystallization from an aqueous alcohol, and further optional purification by sublimation, the final product is substantially homogeneous by High Pressure Liquid Chromatography (HPLC) or thin layer chromatographic analysis.

The present invention provides a simple, convenient, safe, and economical method for synthesis of pharmaceutically pure 3,5-dibromosalicylic acid. Liquid bromine is slowly added to an aqueous alcohol solution containing salicylic acid. Slow addition is advised because the bromination reaction is exothermic, and it is desirable to permit only a gradual temperature rise over the approximately 2 hour reaction course required to reach completion. It is common practice in the prior art to conduct a bromination reaction in very dilute bromine concentrations to reduce formation of 2,4,6-tribromophenol: however, in the present method bromine is added in a final molar ratio of 2:1. Under these reaction conditions virtually no mono-brominated contaminants or 2,4,6-tribromophenol are detected.

The initial temperature is typically about 0° C. with a gradual temperature rise over approximately two hours. The starting temperature is not critical so long as the temperature of the reaction mix is not allowed to exceed 40° C. The final temperature is maintained at about 34°. While it is desirable to maintain the temperature below 35° in order to avoid decarboxylation, maintaining the temperature too low, say, at below 20° has no effect in preventing side reactions, and results in slow reaction kinetics.

The bromination reaction of the present method is carried out in aqueous alcohol. Typical alcohols are methanol, ethanol, propanol, and isopropanol. Use of higher alcohols is less advantageous because of their high boiling points and difficulty of removal. The lower alcohols having a boiling point less than about 100° C. are preferred. The presence of water during the reaction dramatically affects the solubility of the desired 3,5-dibromosalicylic acid, causing it to precipitate preferentially immediately upon formation. So rapid is clearance of the product from solution that there is no opportunity for additional bromination to occur with accompanying decarboxylation. Water is included in an amount sufficient to alter the solubility properties of the alcohol medium so as to cause substantially quantitative precipitation of the product. The range of water content is 5 to 50 percent, preferably about 20 percent.

The precipitated 3,5-dibromosalicylic acid product may conveniently be recovered by centrifugation, or, preferably filtration, washed several times in the medium or water, and further purified by recrystallization. In this step, the precipitate is first resolubilized, and then recrystallized from aqueous alcohol. The resultant powder can then be further purified to ultrapure pharmaceutical grade by subliming at a temperature in excess of 180° C. The sublimate is then removed from condensing means such as a cooling tower containing condensing baffles. The purified material can readily be converted to salt derivatives by conventional techniques. The compound of the present invention encompasses all such salt equivalents including, but not limited to, sodium, potassium, copper, and ammonium.

In formulating a topical preparation containing 3,5-dibromosalicylic acid, a lotion, powder, or ointment format may be selected taking into account the type of lesion or skin condition being treated. A typical preparation will contain between about 0.1 and 3.0 percent 3,5-dibromosalicylic acid or its salts in combination with other medicaments and conventional unguents, salves, carriers, and oils.

Alternatively, the purified product may be used directly in other known pharmaceutical applications, as indicated hereinabove. Such applications include the benefical use of 3,5-dibromosalicylic acid as a promoter of absorption of proteins, peptides, and antibiotics (U.S. Pat. No. 4,470,980), and its use as an adjuvant in rectal antibiotic delivery systems (U.S. Pat. Nos. 4,406,896 and 4,464,363).

Other advantages of the present compound and the method of producing it will be apparent from the Example which follows.

EXAMPLE

To a stirred solution of salicylic acid (122 grams, 0.442 mol) in aqueous methanol (100 ml water in 550 ml methanol) bromine (91.7 ml, 0.895 mol) was added dropwise. The addition required two hours. During the addition, the temperature of the reaction mixture rose to 35°–40° C. with evolution of HBr. After completion of the addition, stirring was continued for 30 minutes. A solution of sodium bisulfite (2.5 grams in 50 ml water) was added to degrade excess bromine. The reaction mixture was cooled to 5° for 4 hours and filtered. The crude mixture was washed with water and air dried. HPLC (RP-8, MeOH/water eluant 70:30) demonstrated that the crude product (235.5 grams, representing a 90 percent yield) was free of salicylic acid and contained only trace quantities of other contaminants. Recrystallization of crude product from aqueous methanol gave 3,5-dibromosalicylic acid (210 gram yield), which sublimed above 180° C. The product was sublimed by heating and the sublimate was recovered from a watch glass by scraping.

That which is claimed is:
1. A purified 3,5-dibromosalicylic acid:
   (a) being substantially homogeneous by chromatographic analysis; and
   (b) which sublimes completely at a temperature greater than 180° C.
2. 3,5 di-bromosalicylic acid produced by a method comprising the steps of:
   (a) reacting bromine with salicylic acid contained in an aqueous alcohol solution; and
   (b) maintaining the temperature of the reaction mixture below about 40° C.
3. A purified 3,5-dibromosalicylic acid produced by a method comprising the steps of:
   (a) reacting bromine with salicylic acid contained in an aqueous alcohol solution;
   (b) maintaining the temperature of the reaction mixture below about 40° C.;

(c) recovering the precipitated product;
(d) washing the precipitated product; and
(e) recrystallizing the resolubilized product.

4. 3,5-dibromosalicylic acid produced by the method of claims 2 or 3, together with the further steps of:
 (a) subliming the product at a temperature greater than 180° C.; and
 (b) condensing the sublimate.

5. The method of producing a purified 3,5-dibromosalicylic acid comprising the steps of:
 (a) adding liquid bromine to an aqueous alcohol solution containing salicylic acid;
 (b) maintaining the temperature of the solution below 40° C. for a time sufficient to allow the reaction to be complete;
 (c) recovering the precipitated product;
 (d) washing the precipitated product; and
 (e) recrystallizing the resolubilized product.

6. The method of producing an ultrapure 3,5-dibromosalicylic acid comprising the steps of the method of claim 5, together with the further steps of:
 (a) subliming the product at a temperature greater than 180° C.; and
 (b) recovering the sublimate from condensing means.

* * * * *

UNITED STATES PATENT AND TRADEMARK OFFICE
CERTIFICATE OF CORRECTION

PATENT NO. : 5,013,866

DATED : May 7, 1991

INVENTOR(S) : Ton That Hai, Deanna J. Nelson

It is certified that error appears in the above-identified patent and that said Letters Patent is hereby corrected as shown below:

Column 1, line 3, the following statement should appear:

--This invention was made with government support under Contract DAMD17-85-C-5194 awarded by the Department of the Army--

Signed and Sealed this

Twenty-ninth Day of September, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 5,013,866

DATED : May 7, 1991

INVENTOR(S) : Ton That Hai, Deanna J. Nelson

It is certified that error appears in the above-identified patent and that said Letters Patent is hereby corrected as shown below:

Title page, section 54, in the title replace "METOHD" with --METHOD--.

column 1, in the title replace "METOHD" with --METHOD--.

Signed and Sealed this

Tenth Day of November, 1992

Attest:

DOUGLAS B. COMER

*Attesting Officer*   Acting Commissioner of Patents and Trademarks